United States Patent
Chang

(10) Patent No.: US 8,365,735 B2
(45) Date of Patent: Feb. 5, 2013

(54) RESPIRATORY MASK INCLUDING AN ADJUSTMENT UNIT

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 534 days.

(21) Appl. No.: 12/610,828

(22) Filed: Nov. 2, 2009

(65) Prior Publication Data

US 2011/0048425 A1 Mar. 3, 2011

(30) Foreign Application Priority Data

Aug. 26, 2009 (TW) ................................ 98128675 A

(51) Int. Cl.
*A62B 18/08* (2006.01)

(52) U.S. Cl. ......... 128/207.11; 128/206.21; 128/206.24; 128/206.27; 128/206.28; 128/207.13

(58) Field of Classification Search ............. 128/206.21, 128/206.24, 206.27, 206.28, 207.11, 207.13
See application file for complete search history.

(56) References Cited

U.S. PATENT DOCUMENTS

| 6,532,961 B1 | 3/2003 | Kwok et al. | |
| 2005/0005940 A1 | 1/2005 | Gunaratnam | |
| 2006/0289010 A1* | 12/2006 | Kwok et al. | 128/207.11 |
| 2007/0044804 A1* | 3/2007 | Matula et al. | 128/206.21 |
| 2008/0135050 A1* | 6/2008 | Hitchcock et al. | 128/207.11 |
| 2009/0223523 A1 | 9/2009 | Chang | |

FOREIGN PATENT DOCUMENTS

| GB | 922077 | 3/1963 |
| JP | 2009-112825 | 5/2009 |
| WO | WO 97/20597 A1 | 6/1997 |
| WO | WO 00/78384 | 12/2000 |
| WO | WO 2007/021777 A2 | 2/2007 |

* cited by examiner

*Primary Examiner* — Loan Thanh
*Assistant Examiner* — Aundria Hairell
(74) *Attorney, Agent, or Firm* — DLA Piper LLP (US)

(57) ABSTRACT

A respiratory mask includes: a mask body including a mask shell, and a mask cushion connected to a rear side of the mask shell; a front cover disposed in front of and hinged to the mask shell, and having a support arm extending upwardly; a forehead support unit having a forehead frame connected to a top end of the support arm, and a forehead pad connected to a rear side of the forehead frame; and an adjustment unit connected to at least one of the mask shell and the front cover, and operable to produce relative movements of the mask shell and the front cover so that the mask body can abut against the user's nose with an appropriate abutment pressure.

6 Claims, 14 Drawing Sheets

RESPIRATORY MASK INCLUDING AN ADJUSTMENT UNIT

CROSS-REFERENCE TO RELATED APPLICATION

This application claims priority of Taiwanese application No. 098128675, filed on Aug. 26, 2009.

BACKGROUND OF THE INVENTION

1. Field of the Invention

This invention relates to a respiratory mask, more particularly to a respiratory mask including an adjustment unit.

2. Description of the Related Art

Referring to FIG. 1, a conventional respiratory mask 11 includes a mask body 111 adapted to cover a user's nose and/or mouth, and a forehead support unit 112 mounted on the mask body 111 for supporting the user's forehead. An air supply tube 13 is connected to the mask body 111 for providing a passage of a positive pressure airflow into the respiratory mask 11.

In use, head straps 14 are respectively inserted through two opposite sides of the forehead support unit 112 and the mask body 111, and extend around a rear side of the user's head. Subsequently, the head straps 14 are tightened so as to respectively secure the forehead support unit 112 and the mask body 111 to the user's forehead and cheeks, such that a central portion of the mask body 111 covers the user's nose and/or mouth to provide an abutment pressure against the root of the nose.

However, strength of the abutment pressure against the root of the nose varies with facial differences, such as forehead shape, cheek shape, and nose shape. For example, when the user has a concave or flat nose shape, there is a weak abutment pressure against the root of the nose that a gas tight seal of the respiratory mask 11 is not achieved, which results in leakage of the airflow. Conversely, the user with a convex or straight nose shape may feel a strong applied abutment pressure and becomes uncomfortable when wearing the respiratory mask 11 for a long period of time. Therefore, the respiratory mask 11 having an invariable size is not suited for accommodating a variety of facial differences among individuals.

U.S. Pat. No. 6,532,961 discloses an adjustable respiratory mask having a structure similar to that of the conventional respiratory mask 11. The adjustable respiratory mask includes a forehead support unit that has a cushion frame abutting against a user's forehead, and a joining member adjustably mounted between a mask body and the forehead support. The joining member is adjustable to change an angle between the cushion frame and the mask body to suit the wearer's forehead topography.

However, such angular adjustment does not alter the abutment pressure against the root of the user's nose.

SUMMARY OF THE INVENTION

Therefore, an object of the present invention is to provide a respiratory mask that can overcome the aforesaid drawbacks associated with the prior art.

According to the present invention, a respiratory mask comprises: a mask body including a mask shell, and a mask cushion connected to a rear side of the mask shell; a front cover disposed in front of and hinged to the mask shell; and having a support arm extending upwardly; a forehead support unit having a forehead frame connected to a top end of the support arm, and a forehead pad connected to a rear side of the forehead frame; and an adjustment unit connected to at least one of the mask shell and the front cover, and operable to produce relative movements of the mask shell and the front cover and to adjust the position of the mask shell relative to the front cover.

BRIEF DESCRIPTION OF THE DRAWINGS

Other features and advantages of the present invention will become apparent in the following detailed description of the preferred embodiments of this invention, with reference to the accompanying drawings, in which.

DETAILED DESCRIPTION OF THE PREFERRED EMBODIMENTS

Figure 1:
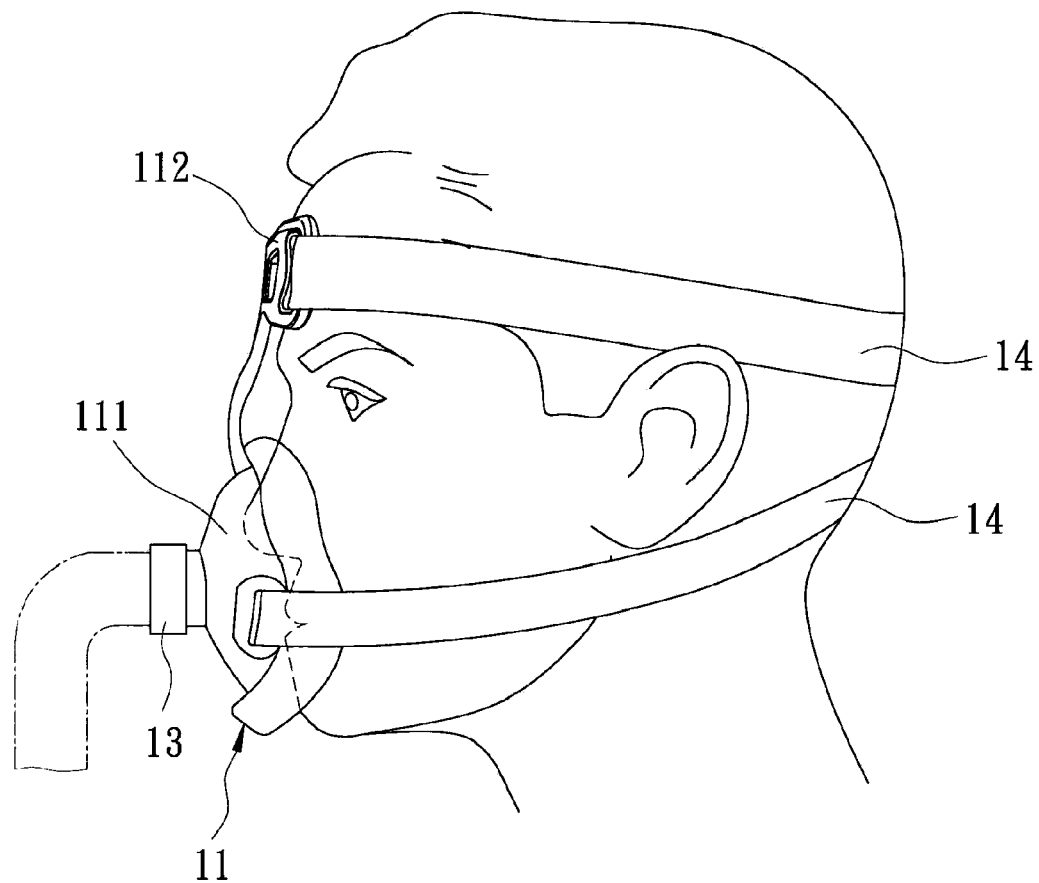
FIG. 1 is a schematic view of a conventional respiratory mask in a state of use.

Before the present invention is described in greater detail with reference to the accompanying preferred embodiments, it should be noted herein that like elements are denoted by the same reference numerals throughout the disclosure.

Figure 2:
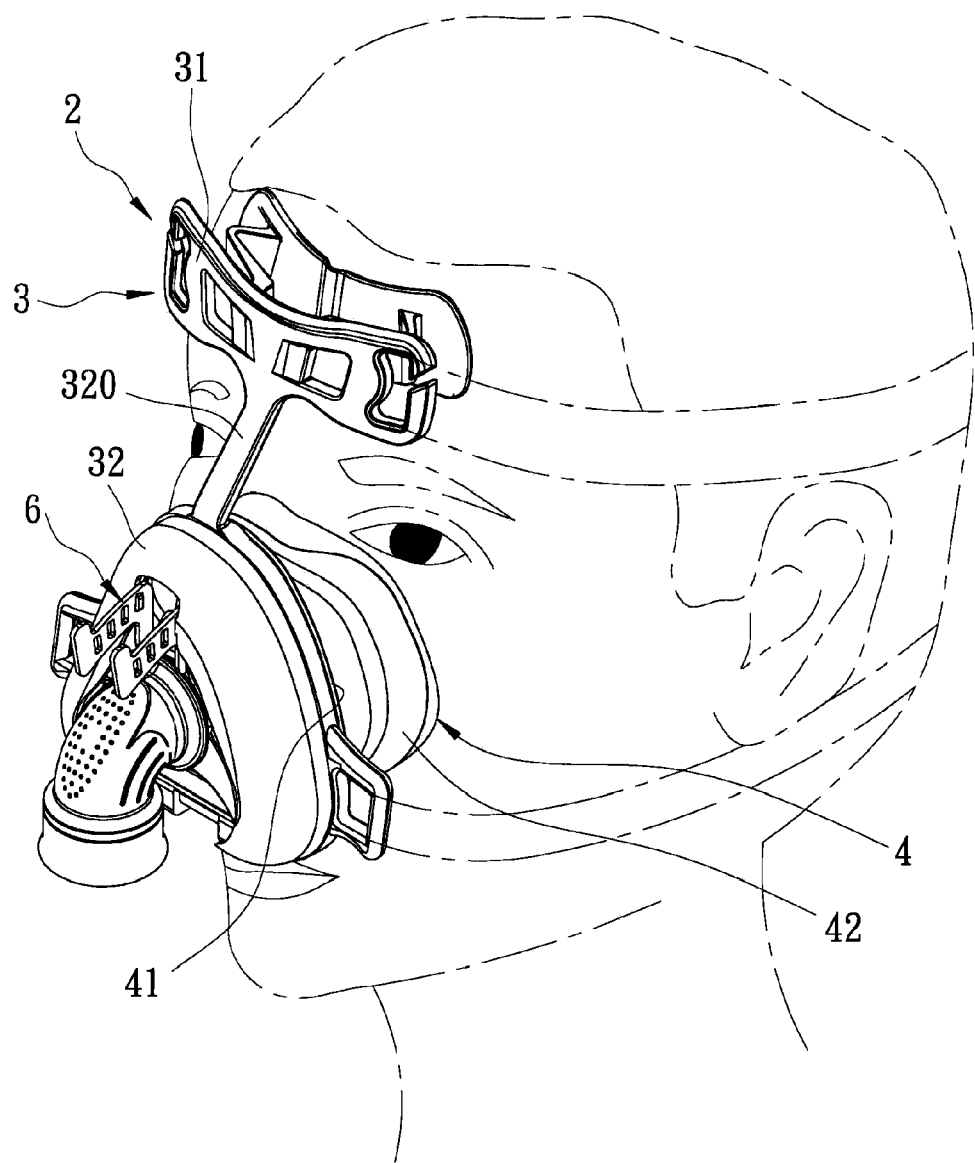
FIG. 2 is a perspective view of the first preferred embodiment of a respiratory mask according to this invention in a state of use.
Figure 3:
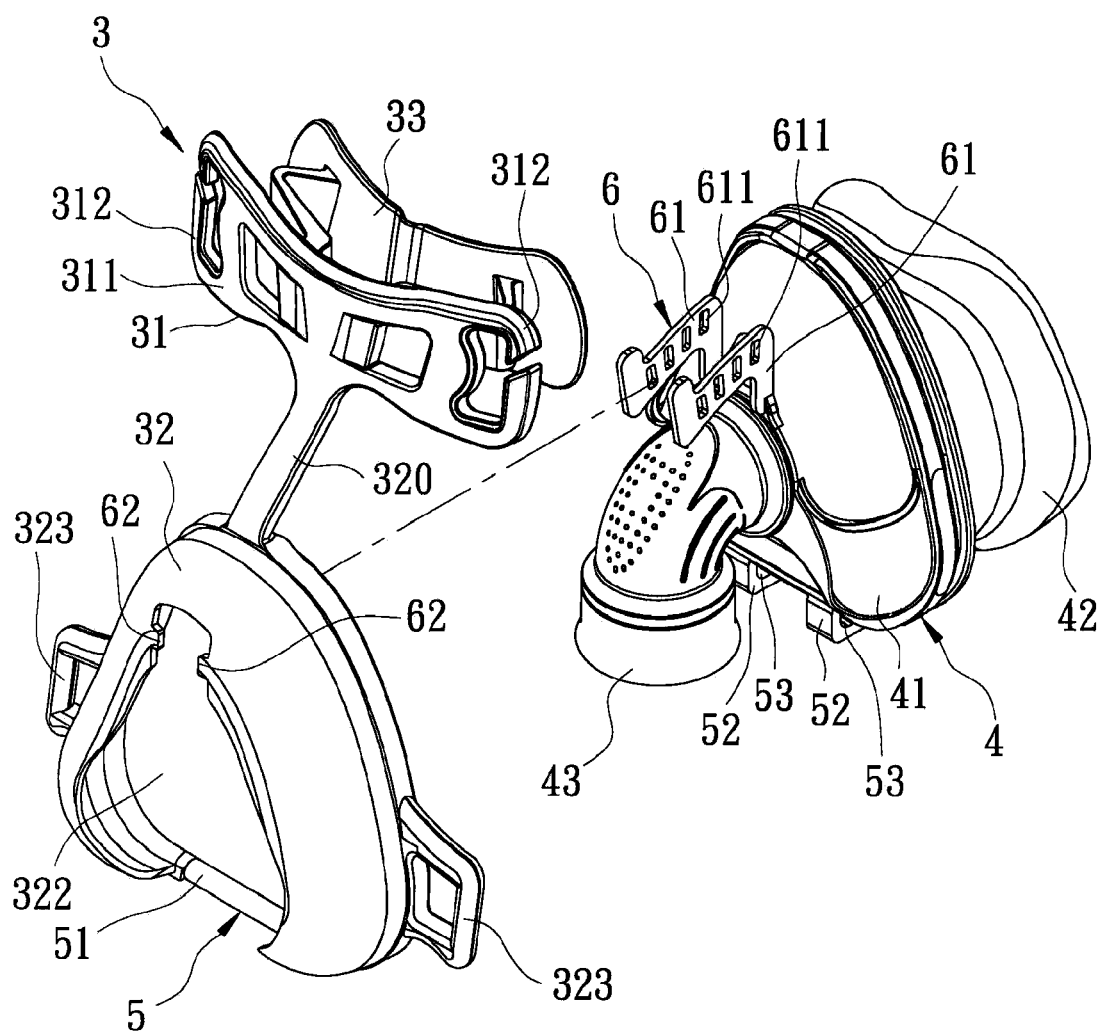
FIG. 3 is an exploded perspective view of the first preferred embodiment.

Referring to FIGS. 2 and 3, a respiratory mask 2 of the first preferred embodiment according to this invention includes a mask body 4, a front cover 32, a forehead support unit 3, a hinge unit 5, and an adjustment unit 6.

The mask body 4 includes a mask shell 41, a mask cushion 42 connected to a rear side of the mask shell 41 and adapted to contact a user's nose and/or mouth, and an air conduit 43 projecting forwardly from the mask shell 41.

The front cover 32 is disposed in front of and is hinged to the mask shell 41, and has a support arm 320 extending upwardly. The front cover 32 further has a mid hole 322 for extension of the air conduit 43 therethrough and two opposite sides respectively provided with a pair of strap connectors 323.

The forehead support unit 3 has a forehead frame 31 and a forehead pad 33 connected to a rear side of the forehead frame 31. The forehead frame 31 has a T-shaped frame part 311 connected to a top end of the support arm 320 and is provided with a pair of slotted connectors 312 on two opposite sides thereof.

The hinge unit 5 includes a hinge pin 51 mounted to a lower part of the front cover 32 in a transverse direction transverse to a front-to-rear direction of the mask shell 41, two hinge seats 52 projecting from a lower part of the mask shell 41, and two insert holes respectively formed in the hinge seats 52 for insertion of the hinge pin 51 therethrough. By virtue of the hinge unit 5, an upper part of the mask shell 41 can be rotated toward and away from an upper part of the front cover 32 so that the mask body 4 can provide a gas tight seal and a comfortable abutment pressure against the user's nose.

The adjustment unit 6 is connected to and disposed on the front cover 32 and the mask shell 41 above the air conduit 43, and is operable to produce relative movements of the upper parts of the mask shell 41 and the front cover 32 so that relative positions of the mask shell 41 and the front cover 32 can be adjusted.

In this embodiment, the adjustment unit 6 includes a pair of adjustment members 61 which project forwardly from the mask shell 41 to extend through the mid hole 322 of the front cover 32, and which are formed as a pair of resilient members. Each of the adjustment members 61 has four adjusting elements that are formed as four locking holes 611 and that are spaced apart from each other in the front-to-rear direction. The front cover 32 further has two tongues 62 protruding into the mid hole 322 and engageable with a selected one of the locking holes 611 in each of the adjustment members 61.

Figure 4:
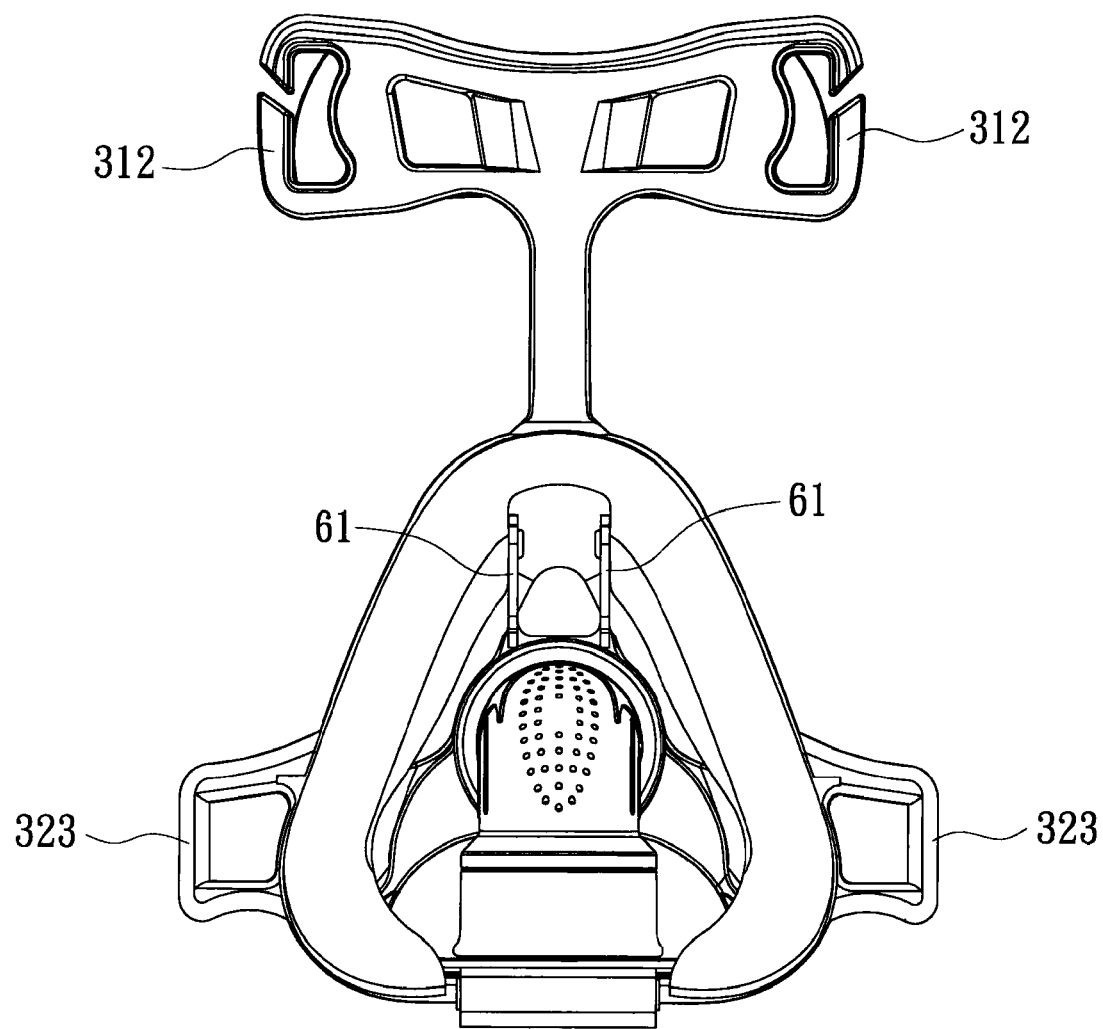
FIG. 4 is a front view of the first preferred embodiment illustrating two resilient members respectively engaged with two tongues.
Figure 5:
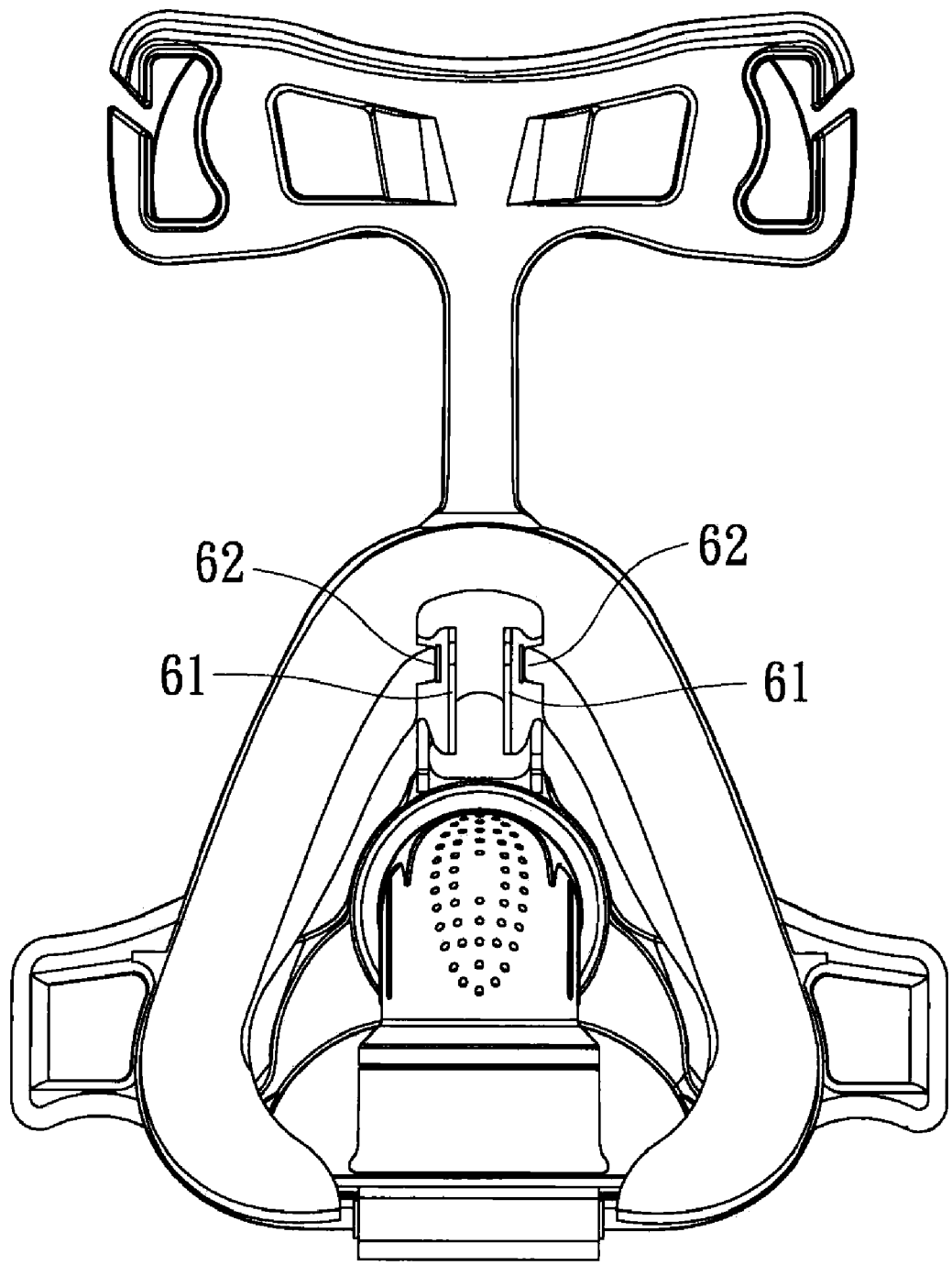
FIG. 5 is the same view as FIG. 4, but illustrating the resilient members disengaged from the tongues.

The adjustment members 61 are movable between a locking position and a non-locking position. Referring to FIG. 4, at the locking position, one of the locking holes 611 in each of the adjustment members 61 engages one of the tongues 62, thereby locking the mask body 4 against movement. Referring to FIG. 5, at the non-locking position, the adjustment members 61 are pressed toward each other to disengage the tongues 62 from respective ones of the locking holes 611 such that the mask body 4 can be rotated about the hinge pin 51 relative to the front cover 32.

Figure 6:
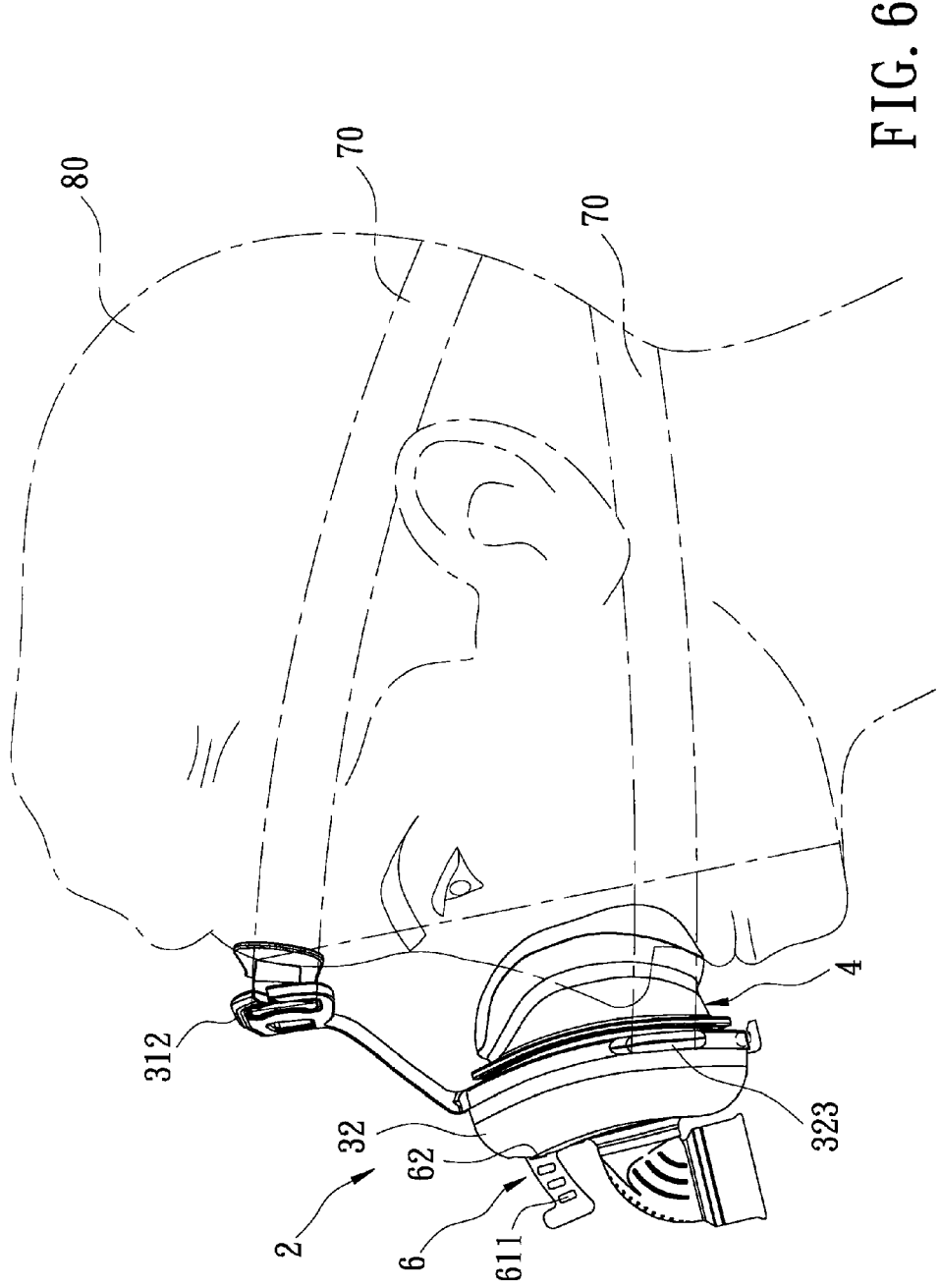
FIG. 6 is a side view of the first preferred embodiment showing that the respiratory mask is used to cover a user's nose and mouth.

Referring to FIG. 6, in use, head straps 70 are inserted respectively through the slotted connectors 312 and the strap connectors 323 and then extend rearwardly around the user's head 80. After adjusting a suitable pulling force to secure the respiratory mask 2 to the user's head 80, the mask body 4 is adjusted to pivot relative to the front cover 32 through the adjustment unit 6 such that an angle formed therebetween can be adjusted, thereby providing an abutment pressure against the root of the user's nose suitable for the facial dimensions of different users.

Figure 7:
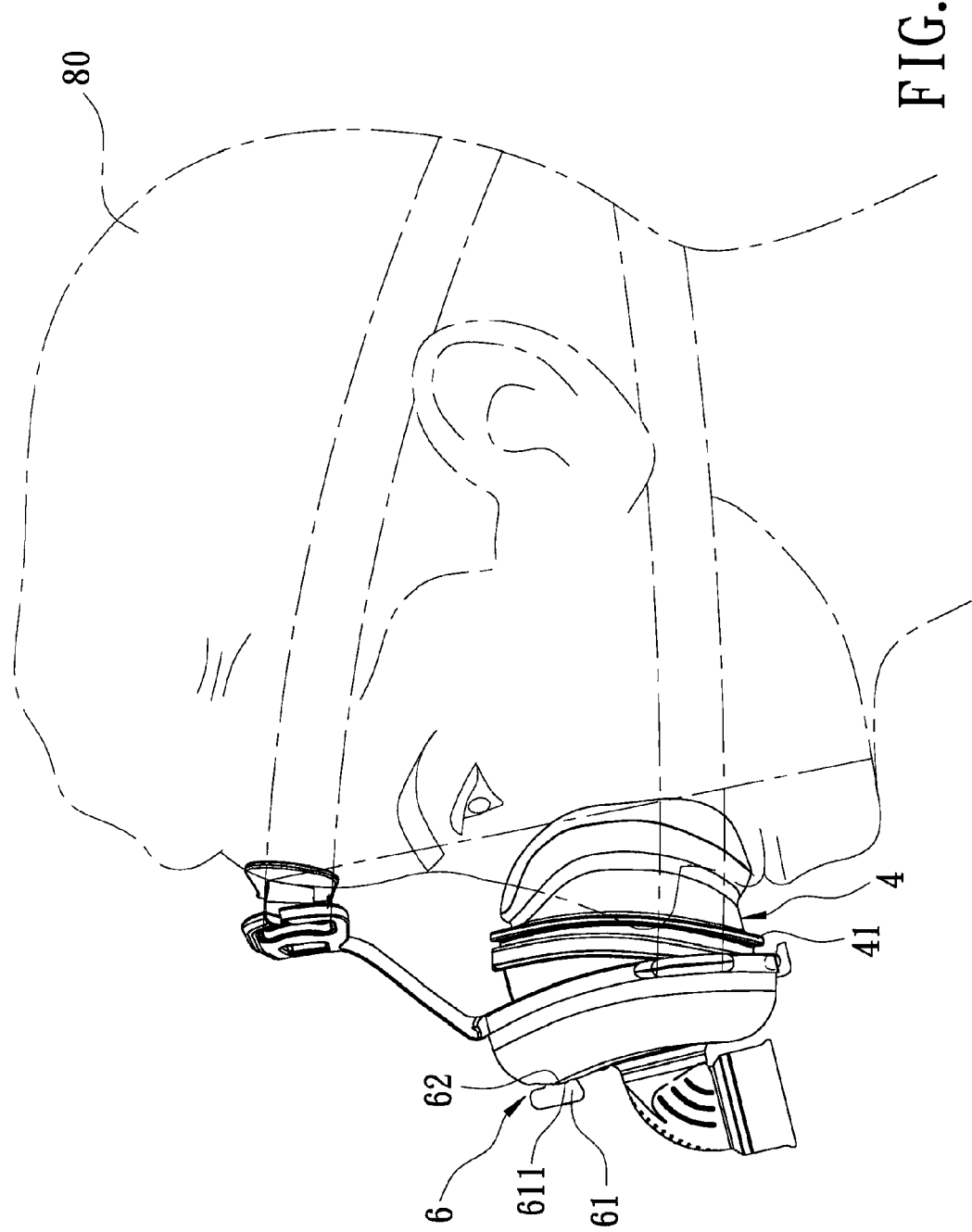
FIG. 7 is the same view as FIG. 6, but illustrating a mask body at a locking position after adjustment.
Figure 8:
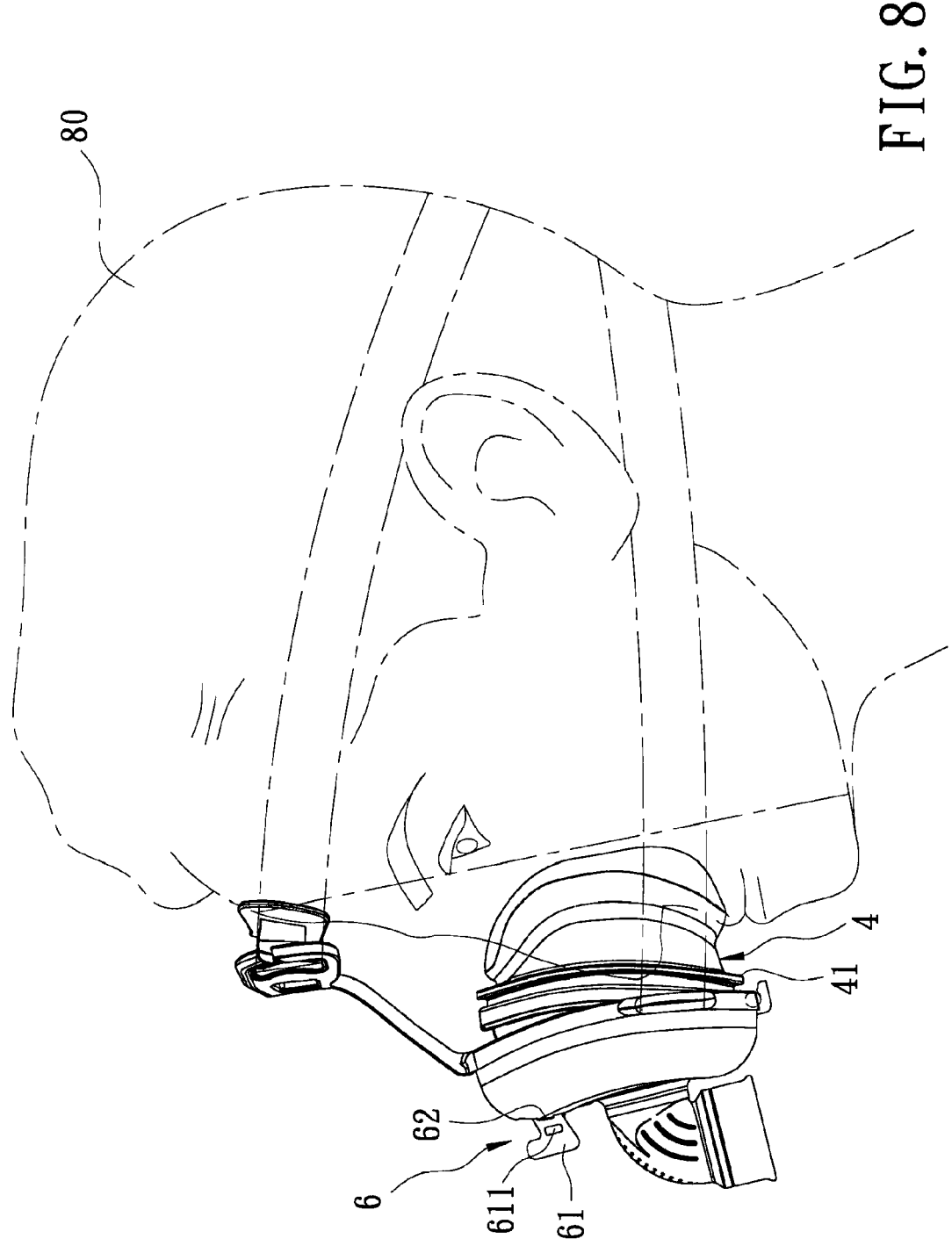
FIG. 8 is the same view as FIG. 6, but illustrating the mask body at another locking position after adjustment.

For example, referring to FIG. 7, the user has a flat nose shape and a relatively high forehead. Referring to FIG. 8, the user has a straight nose shape and a relatively low forehead. In both cases, the adjustment unit 6 is operated to move the upper part of the mask body 4 toward to the user's head 80, and the adjustment members 61 are locked by engaging the respective tongues 62 at the suitable locking holes 611 so that a suitable abutment pressure is provided against the root of the user's nose. It is noted that the locking holes 611 used in the case of FIG. 8 are nearer to the mask shell 41 compared to the locking holes 611 used in the case of FIG. 7.

It is worth mentioning that the relative positions of the mask shell 41 and the front cover 32 are varied depending on the actual requirements.

Figure 9:
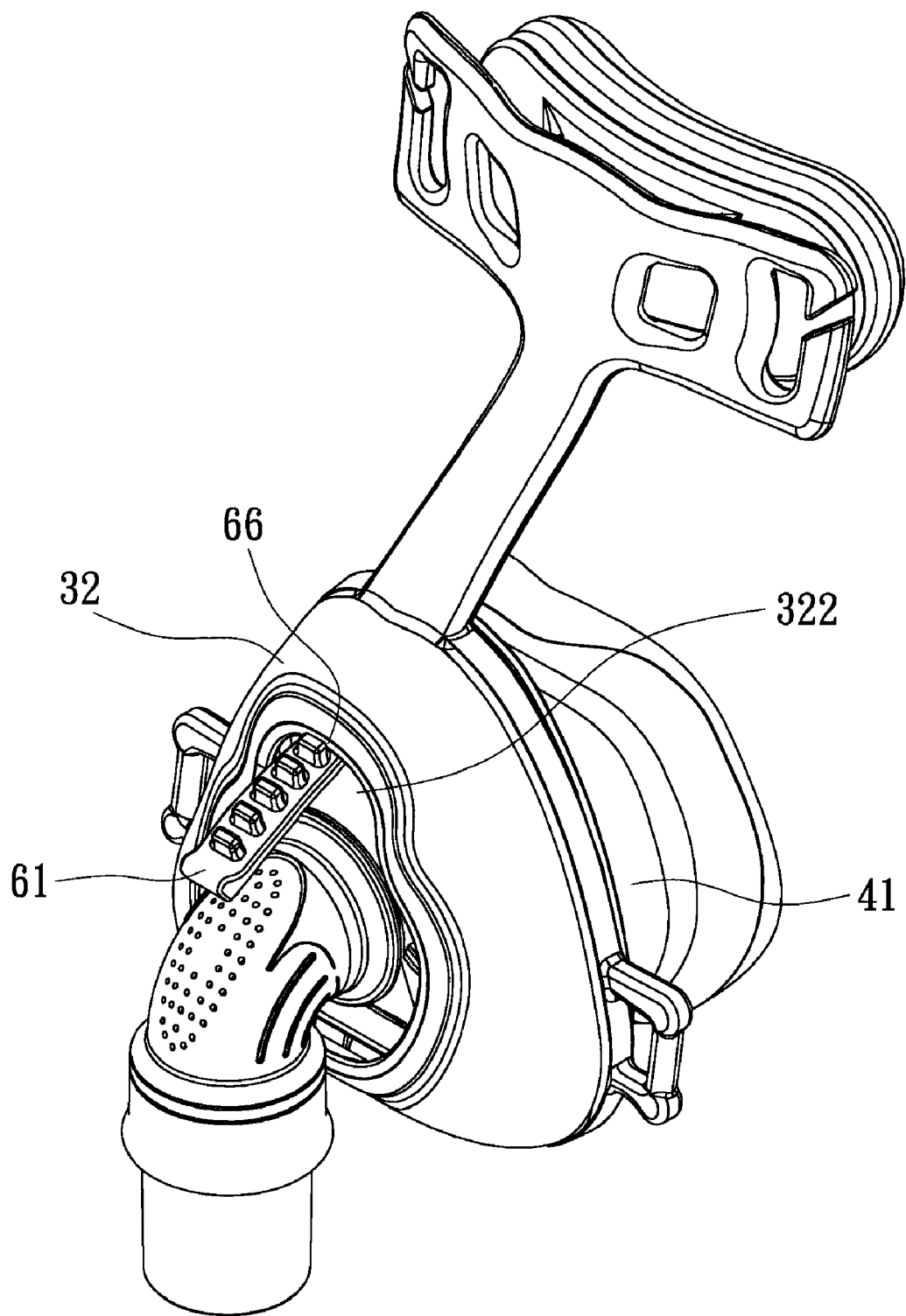
FIG. 9 is an assembled perspective view of the second preferred embodiment of the respiratory mask according to this invention.
Figure 10:
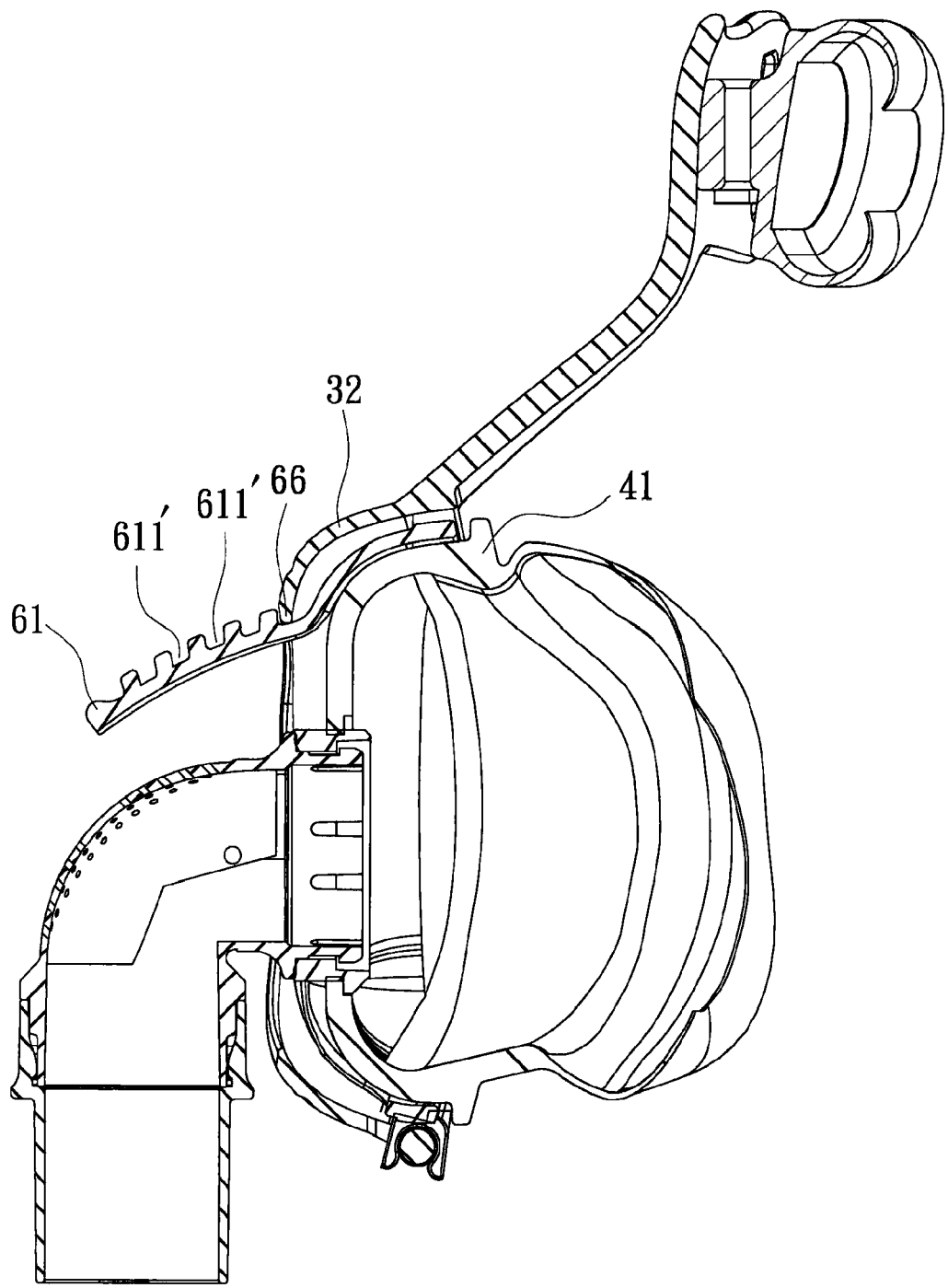
FIG. 10 is an assembled sectional view of the second preferred embodiment.

Referring to FIGS. 9 and 10, the second preferred embodiment of the present invention differs from the first preferred embodiment in that the adjustment member 61 is formed as a single strip member that includes five locking grooves 611' acting as the adjusting elements. The front cover 32 further has an edge part 66 that bounds partially an upper part of the mid hole 322 and that selectively engages one of the locking grooves 611'. The adjustment member 61 is resilient to move downwardly when a force is applied thereon such that the edge part 66 is disengaged from the locking grooves 611' to allow the relative movements of the upper parts of the mask shell 41 and the front cover 32. Subsequently, when the mask shell 41 is adjusted to a desired position, the force is released and the adjustment member 61 moves upwardly to engage the edge part 66 in another of the locking grooves 611', thereby once again locking the mask shell 41 and the front cover 32 against movement.

Figure 11:
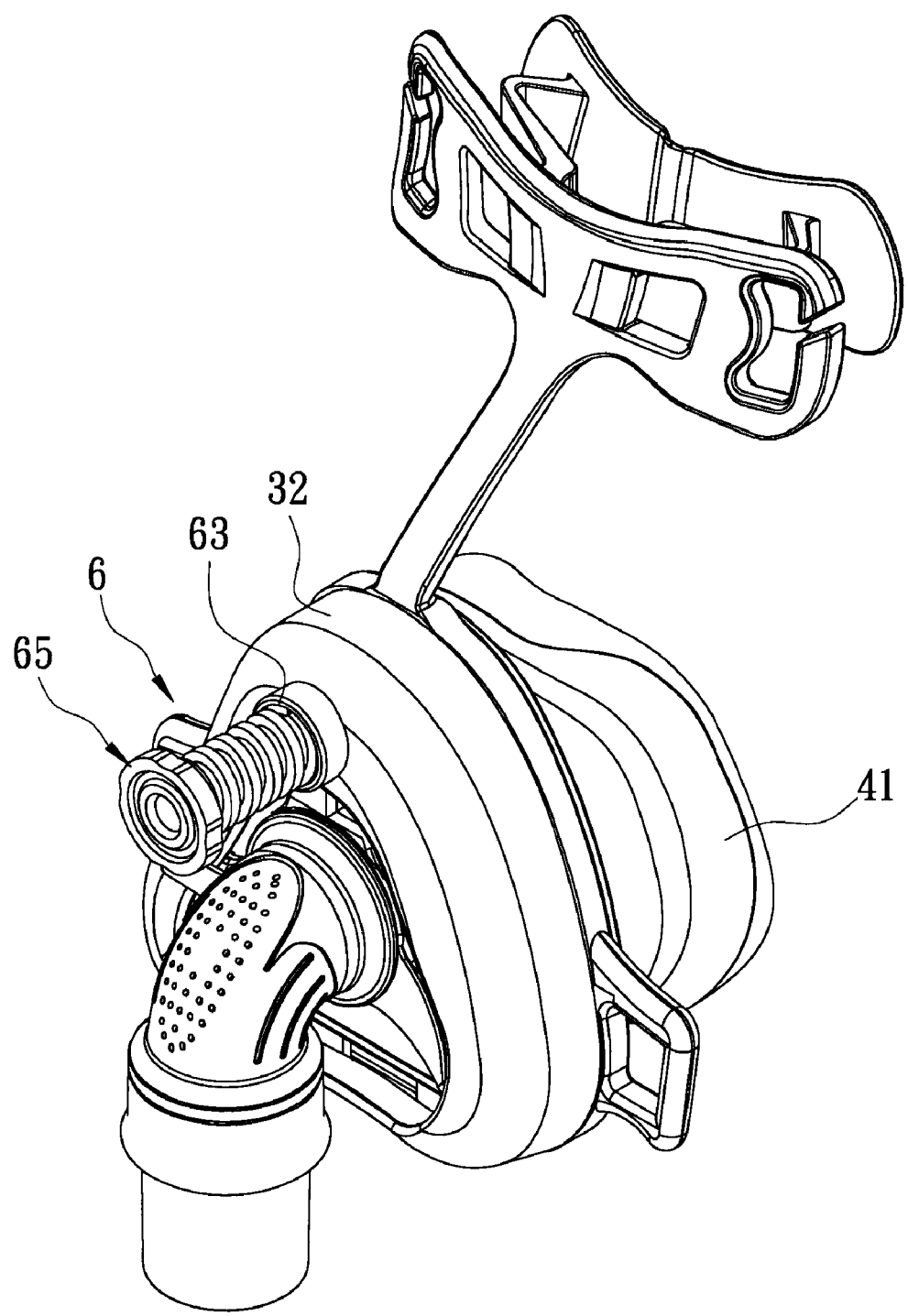
FIG. 11 is an assembled perspective view of the third preferred embodiment of the respiratory mask according to this invention.
Figure 12:
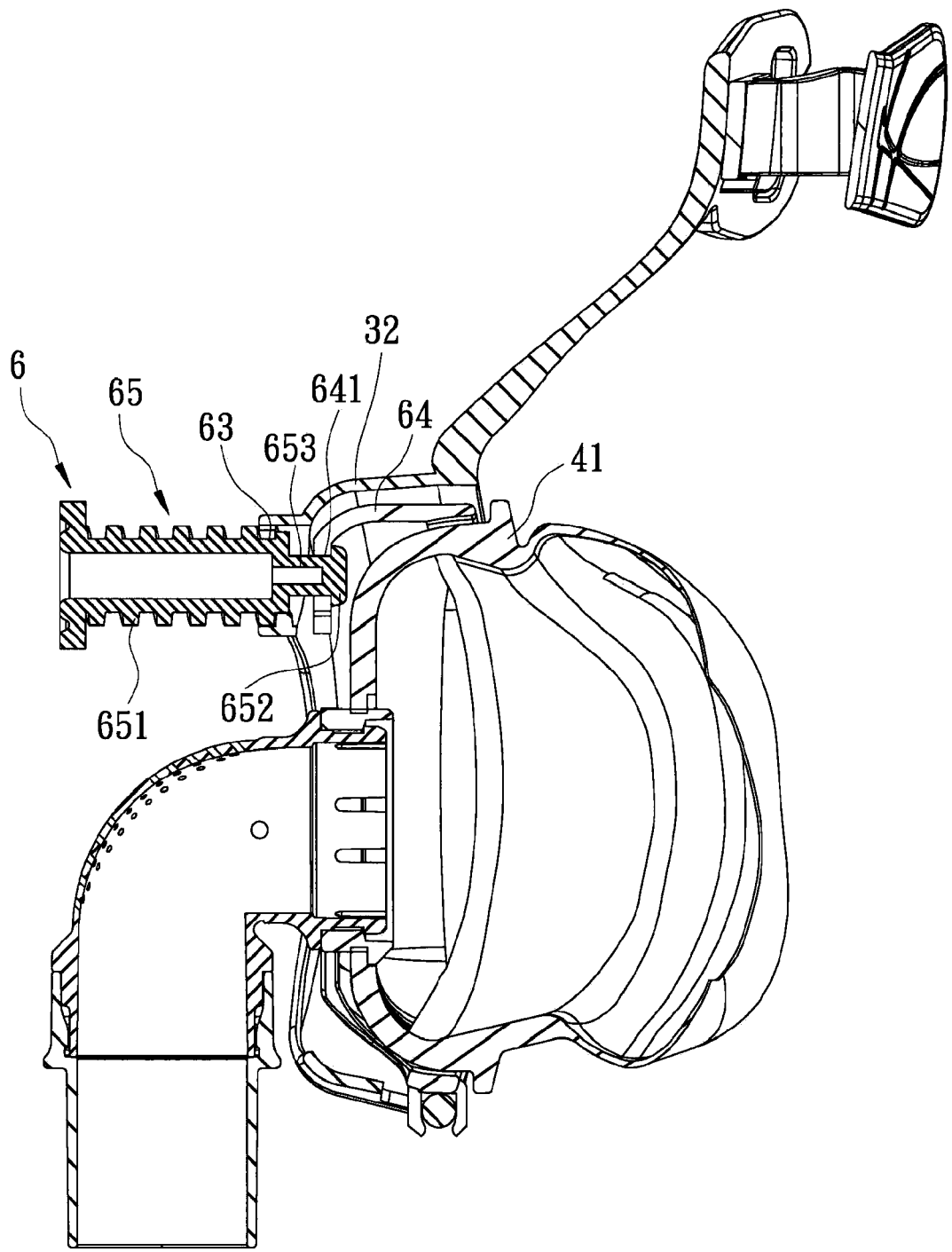
FIG. 12 is an assembled sectional view of the third preferred embodiment.

Referring to FIGS. 11 and 12, the third preferred embodiment of the present invention differs from the first preferred embodiment in that the adjustment unit 6 includes a screw hole 63 provided in the upper part of the front cover 32, a connection member 64 connected to and extending forwardly from the mask shell 41 behind the front cover 32, and a driving screw 65 engaged threadedly to the screw hole 63. The connection member 64 is resilient and has a through hole 641 corresponding in position to the screw hole 63. The driving screw has a screw portion 651, a drive portion 652 extending rearwardly from the driving screw 654 and having a cross-section larger than that of the through hole 641 of the connection member 64, and a middle portion 653 extending between the screw portion 651 and the drive portion 652. The screw portion 651 is engaged threadedly to the screw hole 63, and the middle portion 653 extends through the through hole 641. When the screw portion 651 is rotated in one direction, the drive portion 652 abuts against and pulls the connection member 64 to move forwardly, thereby driving the mask shell 41 to move. Conversely, when the screw portion 651 is rotated in an opposite direction, the drive portion 652 allows the mask shell 41 to move rearwardly.

Figure 13:
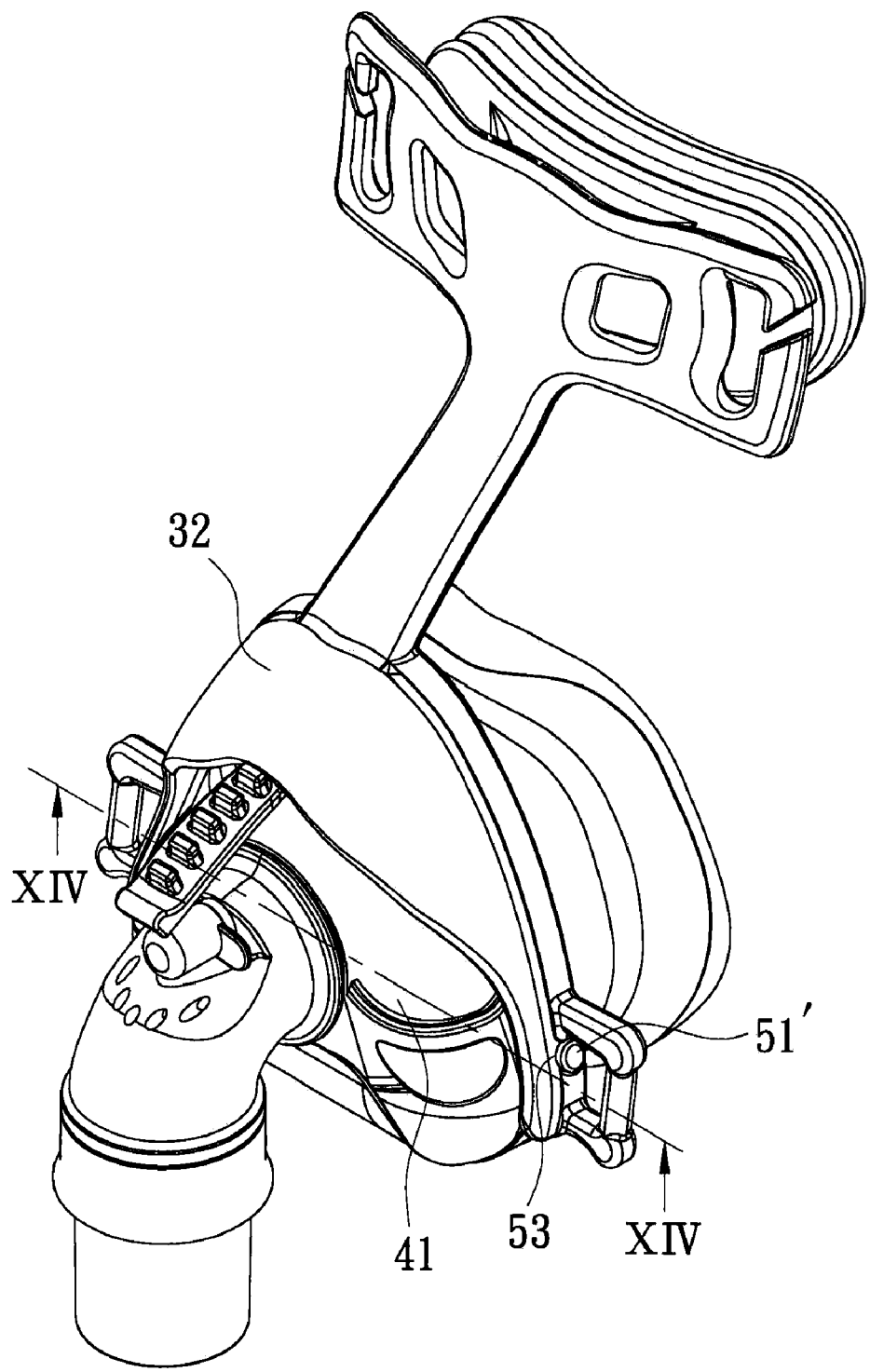
FIG. 13 is an assembled perspective view of the fourth preferred embodiment of the respiratory mask according to this invention.
Figure 14:
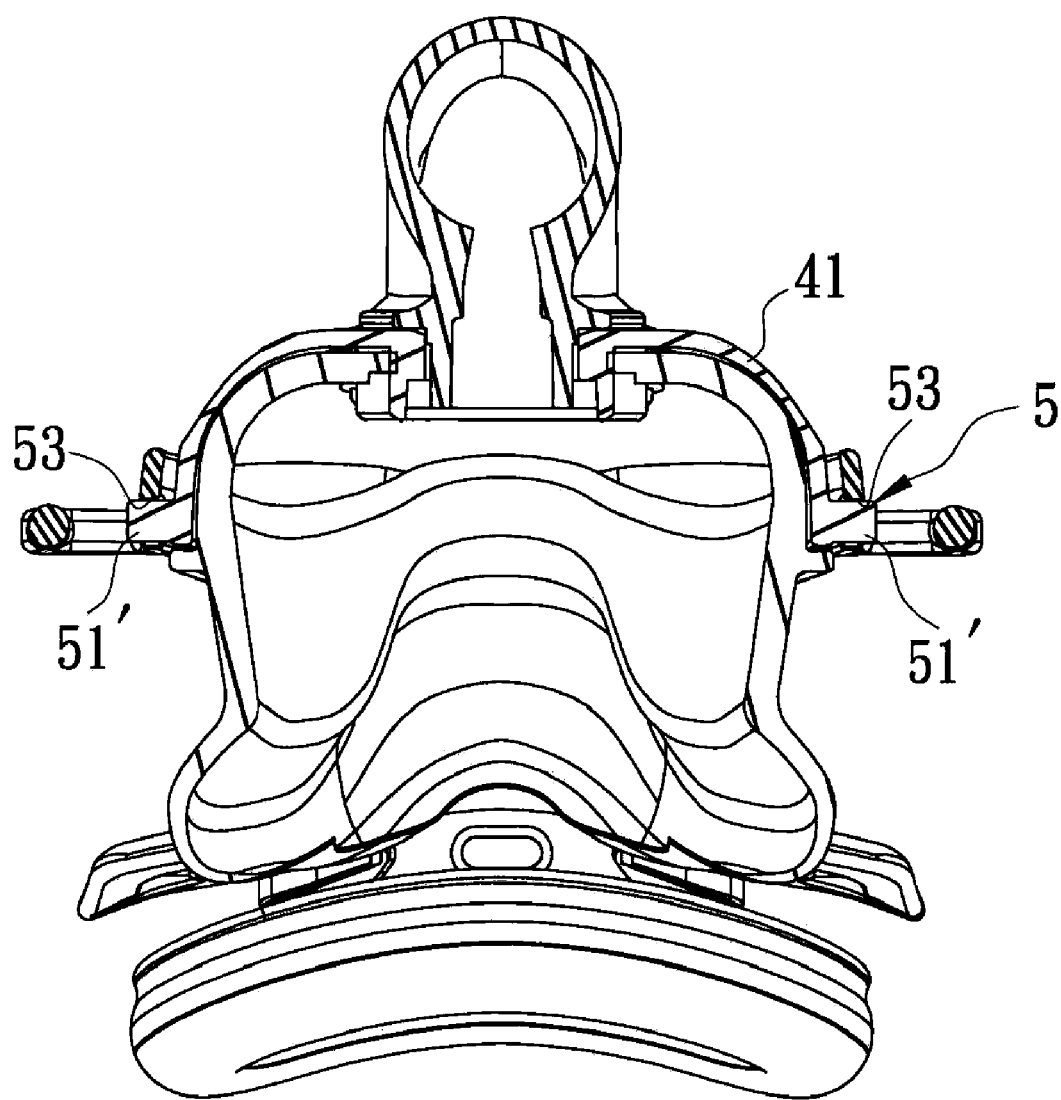
FIG. 14 is a sectional view of the fourth preferred embodiment taken along line XIV-XIV in FIG. 13.

Referring to FIGS. 13 and 14, the fourth preferred embodiment of the present invention differs from the second preferred embodiment in that the front cover 32 has a substantially U-shape. The hinge unit 5 includes two hinge pins 51' extending oppositely from two opposite sides of the mask shell 41 and transverse to the front-to-rear direction, and two insert holes 53 formed respectively in two opposite sides of the front cover 32. The hinge pins 51' extend through the insert holes 53, respectively.

It is worth mentioning that the adjustment unit 6 embodied in the first and third embodiments can also be applied in this embodiment.

By virtue of the hinge unit 5 and the adjustment unit 6, the angle of the mask shell 41 relative to the front cover 32 can be altered so as to provide a comfortable abutment pressure against the root of the user's nose to suit the facial dimensions of different users.

With the invention thus explained, it is apparent that various modifications and variations can be made without departing from the spirit of the present invention. It is therefore intended that the invention be limited only as recited in the appended claims.

What is claimed is:

1. A respiratory mask comprising:
a mask body including a mask shell, and a mask cushion connected to a rear side of said mask shell;
a front cover disposed in front of and hinged to said mask shell, and having a support arm extending upwardly;
a forehead support unit having a forehead frame connected to a top end of said support arm, and a forehead pad connected to a rear side of said forehead frame;
an adjustment unit connected to at least one of said mask shell and said front cover, and operable to produce relative movements of said mask shell and said front cover and to adjust the position of said mask shell relative to said front cover; and
a hinge unit attached to a lower part of said front cover and a lower part of said mask shell, said adjustment unit is operable to move upper parts of said front cover and said mask shell away from or toward each other;
wherein said front cover has a mid hole, said mask shell has an air conduit projecting forwardly from said mask shell and extending through said mid hole of said front cover, and said adjustment unit is disposed on said front cover and said mask shell above said air conduit; and
wherein said adjustment unit includes at least one adjustment member which projects forwardly from said mask shell to extend through said mid hole of said front cover and which has a plurality of adjusting elements that are spaced apart from each other in a front-to-rear direction, said front cover being engageable with a selected one of said adjusting elements.

2. The respiratory mask of claim 1, wherein said hinge unit includes a hinge pin mounted to said lower part of said front cover in a transverse direction transverse to a front-to-rear direction of said mask shell, at least one hinge seat projecting from said lower part of said mask shell, and at least one insert hole formed in said hinge seat for insertion of said hinge pin therethrough.

3. The respiratory mask of claim 1, wherein said front cover further has two opposite sides respectively provided with a pair of strap connectors.

4. The respiratory mask of claim 1, wherein said adjustment unit includes a pair of said adjustment members which are formed as a pair of resilient members each having a plurality of locking holes acting as said adjusting elements, said front cover further having two tongues protruding into said mid hole, said resilient members being movable between a locking position, where one of said locking holes in each of said resilient members engages one of said tongues, and a non-locking position, where said resilient members are pressed toward each other to disengage said tongues from respective ones of said locking holes.

5. The respiratory mask of claim 1, wherein said hinge unit includes two hinge pins extending oppositely from two opposite sides of said mask shell and transverse to a front-to-rear direction, and two insert holes formed respectively in two opposite sides of said front cover, said hinge pins extending through said insert holes, respectively.

6. A respiratory mask comprising:
a mask body including a mask shell, and a mask cushion connected to a rear side of said mask shell;
a front cover disposed in front of and hinged to said mask shell, and having a support arm extending upwardly;
a forehead support unit having a forehead frame connected to a top end of said support arm, and a forehead pad connected to a rear side of said forehead frame;
an adjustment unit connected to at least one of said mask shell and said front cover, and operable to produce relative movements of said mask shell and said front cover and to adjust the position of said mask shell relative to said front cover, said adjustment unit being operable to move upper parts of said front cover and said mask shell away from or toward each other;
wherein said front cover has a mid hole, said mask shell has an air conduit projecting forwardly from said mask shell and extending through said mid hole of said front cover, and said adjustment unit is disposed on said front cover and said mask shell above said air conduit; and
wherein said adjustment unit includes a pair of adjustment members which are formed as a pair of resilient members each having a plurality of locking holes acting as adjusting elements that are spaced apart from each other in a front-to-rear direction and which project forwardly from said mask shell to extend through said mid hole of said front cover, said front cover further having two tongues protruding into said mid hole, said resilient members being movable between a locking position, where one of said locking holes in each of said resilient members engages one of said tongues, and a non-locking position, where said resilient members are pressed toward each other to disengage said tongues from respective ones of said locking holes.

* * * * *